United States Patent
Itsuji

(10) Patent No.: US 8,618,486 B2
(45) Date of Patent: Dec. 31, 2013

(54) IMAGE FORMING APPARATUS

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 13/406,491

(22) Filed: Feb. 27, 2012

(65) Prior Publication Data

US 2012/0223229 A1    Sep. 6, 2012

(30) Foreign Application Priority Data

Mar. 4, 2011   (JP) ................................. 2011-047735

(51) Int. Cl.
*G01N 21/00* (2006.01)

(52) U.S. Cl.
USPC ...................... 250/341.1; 250/330

(58) Field of Classification Search
USPC .............................. 250/330, 341.1
See application file for complete search history.

(56) References Cited

U.S. PATENT DOCUMENTS

| | | | |
|---|---|---|---|
| 5,623,145 A | 4/1997 | Nuss | 250/330 |
| 5,710,430 A | 1/1998 | Nuss | 250/358.1 |
| 6,448,553 B1 | 9/2002 | Itsuji et al. | |
| 6,723,991 B1* | 4/2004 | Sucha et al. | 250/341.1 |
| 6,835,925 B2 | 12/2004 | Itsuji et al. | |
| 6,844,552 B2* | 1/2005 | Zhang et al. | 250/338.1 |
| 7,358,918 B2 | 4/2008 | Itsuji | |
| 7,542,000 B2 | 6/2009 | Itsuji | |
| 7,560,695 B2 | 7/2009 | Kasai et al. | |
| 7,570,216 B2 | 8/2009 | Itsuji | |
| 7,633,299 B2 | 12/2009 | Itsuji | |
| 7,745,791 B2 | 6/2010 | Kasai et al. | |
| 7,884,767 B2 | 2/2011 | Itsuji | |
| 7,919,752 B2 | 4/2011 | Itsuji | |
| 7,922,659 B2 | 4/2011 | Itsuji et al. | |
| 7,952,441 B2* | 5/2011 | Koyama et al. | 331/107 T |
| 8,003,961 B2 | 8/2011 | Itsuji | |
| 8,067,739 B2 | 11/2011 | Itsuji | |
| 8,129,683 B2 | 3/2012 | Itsuji et al. | |
| 2002/0067480 A1* | 6/2002 | Takahashi | 356/317 |
| 2005/0162658 A1* | 7/2005 | Pepper | 356/451 |
| 2007/0215810 A1* | 9/2007 | Kurosaka et al. | 250/358.1 |

(Continued)

FOREIGN PATENT DOCUMENTS

JP    3387721    3/2003

OTHER PUBLICATIONS

Chan et al., "A Single-Pixel Terahertz Imaging System Based on Compressed Sensing", Applied Physics Letters 93, 121105 (2008).

*Primary Examiner* — Marcus Taningco
(74) *Attorney, Agent, or Firm* — Fitzpatrick, Cella, Harper & Scinto

(57) ABSTRACT

An apparatus visualizing internal information of an object includes a detection unit of terahertz wave, a generating unit of a time waveform of the terahertz wave, a modulation unit, an adjustment unit, and an addition unit. The modulation unit sequentially performs spatial modulation on a propagation distance for each pixel of a terahertz wave corresponding to a pixel in a horizontal direction by using a plurality of modulation patterns, and emits a plurality of terahertz waves. Based on a time amount converted from the change of the propagation distances corresponding to the modulation patterns, the adjustment unit adjusts a position on a time axis of the time waveforms of a plurality of terahertz waves and calculates a new plurality of time waveforms. The addition unit adds a new time waveform for each pixel. The apparatus can suppress reduction in signal intensity of a terahertz wave while maintaining detection sensitivity.

7 Claims, 9 Drawing Sheets

(56) References Cited

U.S. PATENT DOCUMENTS

| | | | |
|---|---|---|---|
| 2007/0252992 A1* | 11/2007 | Itsuji | 356/369 |
| 2007/0279136 A1* | 12/2007 | Koyama et al. | 331/107 T |
| 2007/0279143 A1* | 12/2007 | Itsuji | 331/185 |
| 2008/0048678 A1* | 2/2008 | Kurosaka et al. | 324/639 |
| 2008/0116374 A1* | 5/2008 | Ouchi et al. | 250/306 |
| 2010/0252738 A1 | 10/2010 | Kasai et al. | |
| 2010/0288928 A1 | 11/2010 | Katagiri et al. | |
| 2012/0112844 A1 | 5/2012 | Sekiguchi et al. | |

* cited by examiner

IMAGE FORMING APPARATUS

BACKGROUND OF THE INVENTION

1. Field of the Invention

The present invention relates to an image forming apparatus and an image forming method using a terahertz wave, and more particularly to an apparatus and a method for visualizing or imaging information in a horizontal direction and a depth direction of an object based on a principle of an apparatus for measuring a terahertz wave in a time domain, i.e. terahertz time domain spectroscopy system (THz-TDS system).

2. Description of the Related Art

A terahertz wave is an electromagnetic wave having a component of a frequency band in a range of 0.03 THz or more and 30 THz or less. These frequencies contain many wavelengths which various substances such as biological molecules specifically absorb depending on their structure and condition. Taking advantage of these features, there has been developed an inspection technique for performing non-destructive material analysis and identification using a terahertz wave. Also, a terahertz wave is expected to be applied to a safe imaging technique as an alternative to an X-ray imaging technique as well as a high-speed communication technique.

In many cases, a terahertz wave having a shape of subpicosecond pulse is used for the above applications. In general, however, it is difficult to acquire such a pulse in real time. In light of this, a THz-TDS system performs sampling measurement by ultrashort pulse light (also referred to as excitation light in the present description) having a pulse width in the order of femtoseconds. This terahertz wave sampling is achieved by adjusting a time difference between a time when excitation light reaches a generation unit for generating a terahertz wave and a time when the excitation light reaches a detection unit for detecting the terahertz wave. For example, a stage having a folded optical system (also referred to as a delay optical unit in the present description) is inserted in a propagation path of an excitation light and an amount of folding of the excitation light is adjusted to acquire the time difference. In many cases, the generation unit or the detection unit is implemented by a photoconductive element including an antenna electrode pattern having a small gap formed on a semiconductor film.

When an object is imaged based on the principle of a THz-TDS system, a position of the terahertz wave irradiating the object is moved relatively in the surface direction with respect to the object. Imaging is attempted by measuring a time waveform of a terahertz wave for each pixel forming an image (see Japanese Patent No. 3387721). Such a system, however, needs to sequentially mechanically perform raster scanning on the places to be measured for each pixel, whereby it takes time to image the object. In order to solve this problem, there has been disclosed a method of collectively acquiring the time waveform of a plurality of pixels using one photoconductive element (see Appl. Phys. Lett. 93, 121105 (2008)). In this method, an object is irradiated with a terahertz wave of a substantially collimated form and a terahertz wave from the object is subjected to spatial modulation by a metal opening pattern corresponding to a pixel. When the metal opening is opened, the terahertz wave is transmitted therethrough, but when the metal opening is closed, the terahertz wave is reflected thereby, whereby a spatial distribution depending on the presence or absence of a terahertz wave changes according to the opening pattern. Thus, in an imaging step, a change in this metal opening pattern is monitored to extract each pixel signal based on the spatial distribution of the terahertz wave.

SUMMARY OF THE INVENTION

According to the technique disclosed in the above document: Appl. Phys. Lett. 93, 121105 (2008), a metal opening pattern is used in a step of performing spatial modulation on a terahertz wave. Thus, the signal of some terahertz waves is reflected by a shielding portion of the metal opening pattern, whereby the signal intensity of the terahertz wave reaching a detector is reduced.

In view of the above problem, an apparatus of the present invention for visualizing internal information of an object using time-domain spectroscopy includes the following components. The apparatus includes a detection unit configured to detect a terahertz wave from the object; a generating unit configured to generate a time waveform of the terahertz wave from an output of the detection unit; a modulation unit configured to sequentially perform spatial modulation of terahertz waves for each pixel, on a propagation distance from an emission of the terahertz waves until reaching the detection unit, by using a first modulation pattern and a second modulation pattern, wherein the terahertz waves each correspond to a pixel of an object in a direction substantially perpendicular to a direction in which the terahertz wave penetrates inside the object, and to emit a first terahertz wave and a second terahertz wave; an adjustment unit configured to convert a change amount of the propagation distance of the terahertz wave for each pixel corresponding to the modulation pattern to a time amount, to adjust positions on a time axis of a first time waveform of the first terahertz wave and a second time waveform of the second terahertz wave from the generating unit based on the time amount, and to generate a third time waveform and a fourth time waveform; and an addition unit configured to perform an addition processing of the third time waveform and the fourth time waveform for each pixel.

Further, in view of above problem, a method of the present invention for visualizing internal information of an object using time-domain spectroscopy has the following steps. The method includes at least a detection step of detecting a terahertz wave from the object by a detection unit; a waveform generating step of generating a time waveform of the terahertz wave from an output of the detection unit in the detection step; a modulation step of sequentially performing spatial modulation of terahertz waves for each pixel, on a propagation distance from an emission of the terahertz waves until reaching the detection unit, by using a first modulation pattern and a second modulation pattern, wherein the terahertz waves each correspond to a pixel of an object in a direction substantially perpendicular to a direction in which the terahertz wave penetrates inside the object, and emitting a first terahertz wave and a second terahertz wave; an adjustment step of converting a change amount of the propagation distance of the terahertz wave for each pixel corresponding to the modulation pattern to a time amount, adjusting positions on a time axis of a first time waveform of a first terahertz wave and a second time waveform of a second terahertz wave generated in the waveform generating step based on the time amount, and calculating a third waveform and a fourth time waveform; and an addition step of performing an addition processing of the third time waveform and the fourth time waveform for each pixel.

The apparatus and the method of the present invention perform terahertz wave spatial modulation by changing the time required for the terahertz wave to reach the detection unit for each pixel, instead of using a spatial distribution based on the presence or absence of the terahertz wave. Thus, since the terahertz wave is not shielded for the spatial modulation, reduction in signal intensity of the terahertz wave can be suppressed, whereby the time waveform of a plurality of pixels can be measured while the detection sensitivity of the terahertz wave is maintained.

Further features of the present invention will become apparent from the following description of exemplary embodiments with reference to the attached drawings.

DESCRIPTION OF THE EMBODIMENTS

Figure 1A:
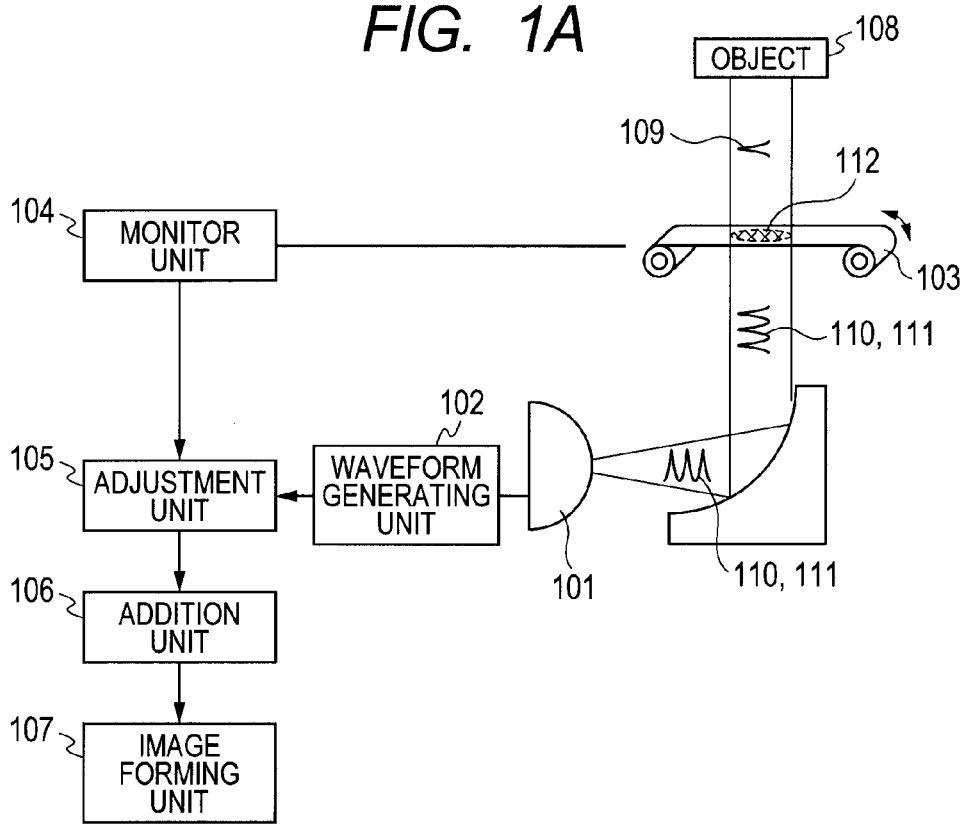
FIG. 1A describes an embodiment of the present invention.

Preferred embodiments of the present invention will now be described in detail in accordance with the accompanying drawings.

In the present invention, specifically, spatial modulations are sequentially performed on a propagation distance of terahertz waves from an emission of the terahertz waves until reaching the detection unit, by using plurality of types of modulation patterns, of which each terahertz wave corresponding to a pixel in a horizontal direction of the object to be visualized, and then a plurality of terahertz waves are emitted. Then, based on a time amount converted from a change amount of a propagation distance of a terahertz wave corresponding to each modulation pattern for each pixel, the position on a time axis of the time waveform of a plurality of terahertz waves outputted by a detection unit is adjusted to generate a plurality of new time waveforms and these time waveforms for each pixel are added.

Embodiments for carrying out the idea of the invention will be described hereinafter with reference to the accompanying drawings. According to FIG. 1A describing an embodiment of the present invention, an apparatus for visualizing internal information of an object using time-domain spectroscopy of the present embodiment includes at least a detection unit 101, a waveform generating unit 102, a modulation unit 103, an adjustment unit 105, and an addition unit 106. Each component will be described below.

(Detection Unit 101)

The detection unit 101 detects a terahertz wave. Detection methods by the detection unit 101 include a method of detecting a change in current from a change in field intensity of the terahertz wave. This method includes a specific method of detecting a change in current corresponding to the field intensity of the terahertz wave by a change in photoconductivity at the time when excitation light is irradiated. An element (also referred to as a photoconductive element in the present description) having an antenna pattern made of a metal electrode on a semiconductor film can be adopted as a device for detecting as such currents.

Methods of detecting an electric field of the terahertz wave using an electro-optical effect and a method of detecting a magnetic field of the terahertz wave using a magneto-optical effect can also be included in the detection methods by the detection unit 101. A device of using a polarization splitter and an electro-optic crystal can be adopted for detecting the electric field using the electro-optical effect. A device of using a polarization splitter and a magneto-optic crystal can be adopted for detecting a magnetic field using a magneto-optical effect. In this embodiment, a photoconductive element will be exemplified as the detection unit 101.

(Waveform Generating Unit 102)

By referring to an output of the detection unit 101, the waveform generating unit 102 generates a time waveform of a terahertz wave. Since, in many cases, the terahertz wave is a pulsed waveform of a picosecond or less, and it is difficult to be obtained in real time. Accordingly, in many cases, sampling measurement is performed by pulsed light having a pulse width shorter than the pulse width of the terahertz wave. In a case in which a photoconductive element is used as the detection unit 101, the pulsed light for use in sampling is the aforementioned excitation light. The excitation light is pulsed light having a pulse width of a femtosecond. The sampling measurement of the terahertz wave is performed by adjusting the timing of the terahertz wave to reach the detection unit 101 and the excitation light to reach the detection unit 101, and in many cases, the time for the excitation light to reach the detection unit 101 is adjusted. The timing of the excitation light can be adjusted by, for example, adjusting the timing that a laser light source generates the excitation light. Specifically, this adjustment can be implemented by a device that modulates a repetition frequency of the laser light source using a signal source for generating a modulation signal. Alternatively, the timing of the excitation light can also be adjusted by, for example, adjusting the timing that the excitation light reaches the detection unit 101 by adjusting the propagation length of the excitation light. Specifically, this adjustment can be implemented by a device of fixing the repetition frequency of the laser light source and mechanically adjusting the propagation length of the excitation light by a stage having a folded optical system (delay optical unit). These devices may be selected as needed according to the specification required for the apparatus such as the image acquisition time for imaging and measurement accuracy. The waveform generating unit 102 monitors the time difference between the terahertz wave and the excitation light each reaching the detection unit 101, and based on the time difference, it plots the output of the detection unit 101 thereby to generate a time waveform of the terahertz wave.

(Modulation Unit 103)

The modulation unit 103 performs spatial modulation on the terahertz wave 109 from the object 108. Specifically, the spatial modulation is performed on pixel information in the horizontal direction of the object 108 whose information is to be imaged. Information of the object to be imaged may include horizontal direction information and depth direction information. The depth direction information refers to information in a direction in which the terahertz wave penetrates inside the object and corresponds to information of the time waveform of the terahertz wave. The horizontal direction information refers to information in a direction substantially perpendicular to the direction in which the terahertz wave penetrates inside the object. In other word, the latter information corresponds to information obtained by fixing, to a certain time, a time axis when the time waveform of the terahertz wave is generated, and monitoring an intensity distribution of the terahertz wave in an observation region. The spatial modulation refers to changing the propagation distance between the object 108 and the detection unit 101 for each pixel to be visualized. In other word, the spatial modulation corresponds to adjusting a propagation time of the terahertz wave for each pixel. The modulation unit 103 includes a modulation region 112 for performing spatial modulation on the terahertz wave 109 from the object.

Figure 1B:
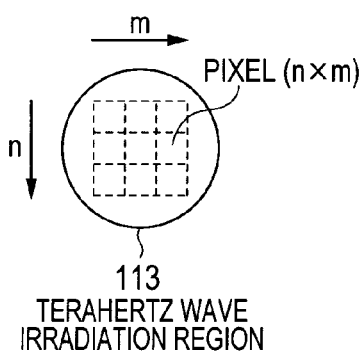
FIG. 1B illustrates an irradiation region of a terahertz wave emitted from an object to a modulation region according to the embodiment of the present invention.

FIG. 1A illustrates an example in which the terahertz wave 109 from the object 108 is transmitted through the modulation region 112 of the modulation unit 103. In this embodiment, as illustrated in FIG. 1B, the irradiation region 113 of the terahertz wave 109 radiating the modulation region 112 from the object includes nine regions corresponding to a pixel for use in visualization, but, apparently, the number of pixel regions not limited thereto. The spatial modulation of the terahertz wave 109 from the object 108 is implemented by a combination of the characteristics of a region corresponding to this pixel. In the present description, the combination of the characteristics of the pixel region is referred to as a modulation pattern. The entire pixel region for use in visualization may be included in the terahertz wave irradiation region 113, or the irradiation region 113 may include only a part of the pixel region for use in visualization. In a case in which the terahertz wave irradiation region 113 includes the entire pixel region to be visualized, whole of the object 108 can be visualized from the output of the detection unit 101. If the terahertz wave irradiation region 113 is smaller than the region to be visualized, it is desirable to add a component in which the position of the object 108 and the terahertz wave 109 is changed relatively in the surface direction within the region to be visualized of the object 108. Then, information of the region to be visualized can be regenerated from the information visualized at each position. For relatively changing the position, the position of the object 108 may be changed, or the terahertz wave 109 from the object may be scanned.

Figure 1C:
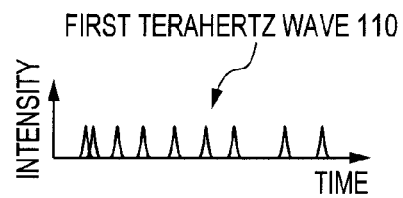
FIG. 1C illustrates a first terahertz wave modulated by a modulation unit.
Figure 1D:
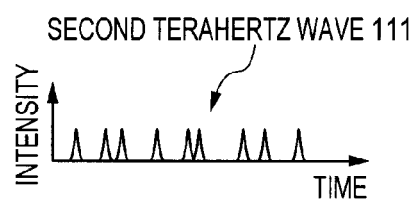
FIG. 1D illustrates a second terahertz wave modulated by a modulation pattern different from the first terahertz wave.

In the example of FIG. 1A, the terahertz wave 109 from the object 108 is an isolated pulse. The terahertz wave 109 from the object is emitted as a pulse train of terahertz waves through the modulation region 112 of the modulation unit 103. The pulse train pattern changes depending on the modulation pattern of the modulation unit 103. In the present description, a terahertz wave emitted through the first modulation pattern is referred to as a first terahertz wave 110. Besides, a terahertz wave emitted through the second modulation pattern is referred to as a second terahertz wave 111. FIGS. 1C and 1D respectively illustrate examples of the first terahertz wave 110 and the second terahertz wave 111. The time interval of the pulse train forming the terahertz waves 110 and 111 changes depending on the modulation pattern of the modulation unit 103. The pulse shape also changes according to the characteristics of the modulation region 112 of the modulation unit 103. In FIG. 1A, when the modulation pattern of the modulation unit 103 changes from the first modulation pattern to the second modulation pattern, the terahertz wave reaching the detection unit 101 changes from the first terahertz wave 110 to the second terahertz wave 111. In a time when the modulation pattern is switched, it is desirable to perform alignment so as not to change the position of each pixel to be visualized. Particularly when the modulation pattern is mechanically switched, it is desirable that an alignment mechanism is accompanied. For example, an encoder or the like is used to detect the position and the position information is used to perform feedback control on the alignment state. Such an embodiment can suppress the image of the visualized object from blurring the boundary, thereby exerting an effect of improving the image contrast.

The above description has focused on a configuration in which the terahertz wave 109 from the object 108 is transmitted through the modulation unit 103, but the present invention is not limited to this configuration. For example, in another configuration of the present invention, the terahertz wave 109 from the object is reflected by the modulation region 112 of the modulation unit 103. Each of FIGS. 2A and 2B, 3A and 3B illustrate a configuration example of the modulation unit 103. The configuration of the modulation unit 103 is not limited thereto, and any configuration may be used as long as spatial modulation can be performed by partially changing the propagation distance of the terahertz wave 109 from the object.

Figure 2A:
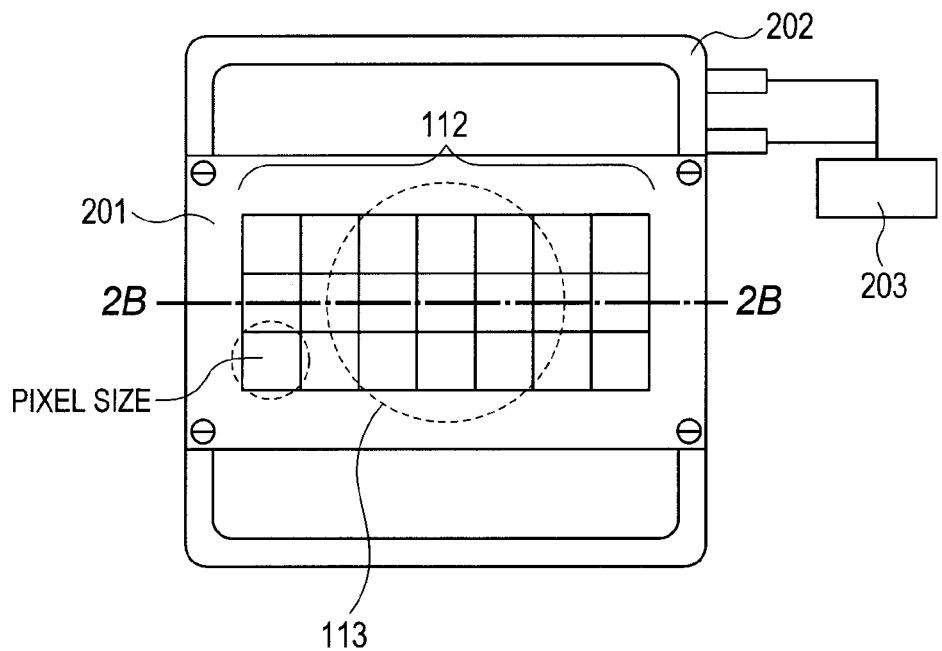
FIG. 2A describes a configuration example of a transmission type modulation unit.

In FIG. 2A, the modulation unit 103 includes a resin sheet 201, a stage 202, and a driver 203. The resin sheet 201 in FIG. 2A includes a modulation region 112 for performing spatial modulation on the terahertz wave 109 from the object 108. The terahertz wave 109 from the object is substantially a collimated beam. Then, the modulation region 112 is substantially diced into a size of a pixel to be visualized. One dice is referred to as a pixel region. Here, the terahertz wave irradiation region 113 is configured to include nine pixel regions.

It has been known that although all elements (corresponding to pixel information) in a wavefront propagate in parallel, the terahertz wave 109 from the object is dissipated with a certain curvature. In other word, the information included in each pixel region of the modulation region 112 is considered to be overlapped with information around each pixel region. When an allowable ratio of a terahertz wave overlapping region between adjacent pixel regions is defined as A(%), an effective distance between the object 108 and the modulation region 112 is desirably set such that the ratio of the overlapping region to be set by a measurer is equal to or less than A. The distance is assumed to be D(m). For example, the terahertz wave 109 from the object is diffracted according to the structure of the object 108 and propagated. Assuming that the beam shape of the terahertz wave 109 from the object can be approximated by a Gaussian beam, the beam diameter of the terahertz wave reaching each pixel region of the modulation region 112 can be approximated by the following expression.

$$w(D) = w_0 [1 + (\lambda D / \pi w_0^2)^2]^{1/2} \qquad \text{expression (1)}$$

In the above expression, $w_0$ refers to a radius of a contour of an intensity of $1/e^2$ of a terahertz wave immediately after emitted from a place of the object 108 corresponding to each pixel region. $w(D)$ refers to a radius of a contour of an intensity of $1/e^2$ of a terahertz wave having a beam diameter $w_0$ propagating by a distance D and being incident on each pixel region. λ refers to a wavelength of the terahertz wave. The size of the pixel region is assumed to be square in which a circle having a radius wo is inscribed. A terahertz wave having a radius w(D) is incident on a pixel region, and the beam diameter of the incident terahertz wave is greater than that of the pixel region. The region extending beyond this pixel region is defined as an overlapping region. Assuming that the beam diameter of the terahertz wave reaching each pixel region from the object 108 extends according to the expression (1), a component of the overlapping region leaks out into adjacent pixel regions, whereby information between the pixel regions is overlapped. When the ratio of the terahertz wave overlapping region from adjacent pixel regions is defined as A for each pixel region, w(D) can be defined by the following expression.

$$w(D)=(1+0.01A)wo \qquad \text{expression (2)}$$

From the expression (1) and the expression (2), a desirable pixel region size 2wo can be calculated by the following expression using a ratio defined by the overlapping region A and the effective distance D from the object 108 to the modulation region 112 of the modulation unit 103. The pixel region size may be a region for covering this 2wo.

$$wo^2 = D\lambda/\{\pi[(1+0.01A)^2-1]^{1/2}\} \qquad \text{expression (3)}$$

For example, assuming that the wavelength λ is 300 μm, the overlapping region A is 20%, and the distance D is 25.4 mm, the desirable pixel region size is about 2 mm×2 mm. The wavelength λ of the terahertz wave to be used herein can be arbitrarily selected from a frequency spectrum of a terahertz wave. For example, the wavelength λ is desirably adjusted to a value near the wavelength having a maximum power. An adjustment of the pixel region size to a wavelength having a maximum sensitivity increases the SN ratio of the signal and improves the contrast of the formed image. As an alternative embodiment, the wavelength λ may be selected according to the desired horizontal resolution. At this time, a wavelength component extending beyond each pixel region is subjected to modulation by an unexpected propagation distance by adjacent pixel regions at spatial modulation. As a result, the signal is diffused, and the diffused component is superimposed as noise at the time waveform adjustment by the adjustment unit 105 to be described later. Then, the diffused component is suppressed by an operation of the addition unit 106 to be described later, and as a result, a differential image with a signal on a low frequency side being suppressed can be acquired.

Figure 9:
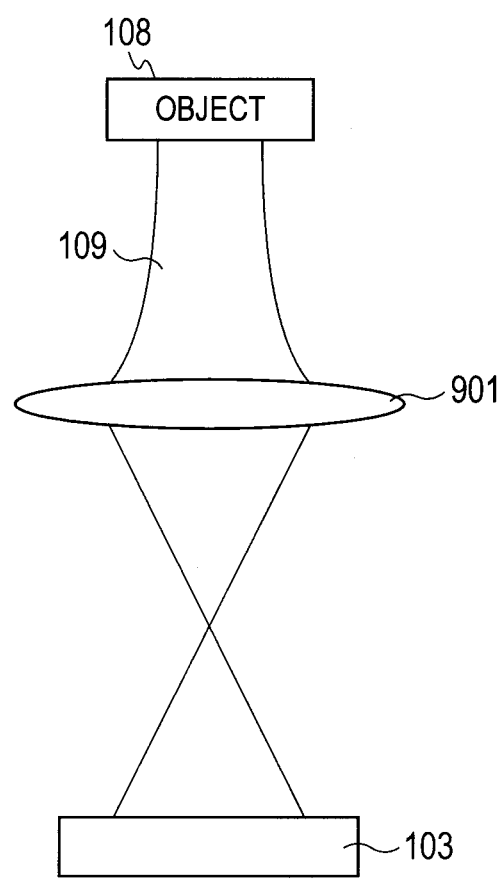
FIG. 9 describes an arrangement of an object 108 and the modulation unit 103.

As is apparent from the expression (3), the pixel region size depends on the distance D. Specifically, the nearer the distance between the object 108 and the modulation region 112, the smaller the pixel region size may be. Ideally, the nearest distance, in other words, being adherent, is desirable. Note that the distance between the object 108 and the modulation region 112 of the modulation unit 103 needs to be greatly increased depending on the required apparatus conditions. At this time, as illustrated by an embodiment in FIG. 9, a light condensing member 901 like a lens may be inserted in between the object 108 and the modulation region 112 of the modulation unit 103 to reproject the image of the object 108 projected on the light condensing member. The light condensing member has a size sufficient for covering the terahertz wave 109 from the object and it is disposed in a position of the aforementioned distance D. The terahertz wave 109 from the object through the light condensing member is reprojected according to the optical characteristics of the light condensing member, and the modulation unit 103 is disposed in a place to be reprojected. Such configuration enables increasing the distance between the object 108 and the modulation region 112 by the distance reprojected by the light condensing member. Thus, this embodiment exerts an effect of improving the apparatus arrangement flexibility.

Each terahertz wave transmitted via each pixel region of the modulation unit 103 has a different propagation distance for reaching the detection unit 101. In other word, the terahertz wave is a set of terahertz wave pulses each having a different propagation time. Consequently, the terahertz wave transmitted via each pixel region can be separated by the position on a time axis even if the propagation region is overlapped with each other. Therefore, the modulation unit 103 and the detection unit 101 can be spaced apart to some extent. The present invention uses an embodiment in which the terahertz wave is condensed and incident on the detection unit 101, and hence the distance may be in a range of establishing this optical system. For example, the distance between the modulation unit 103 and the detection unit 101 is in a range from several 10 to several 100 mm.

Figure 2B:
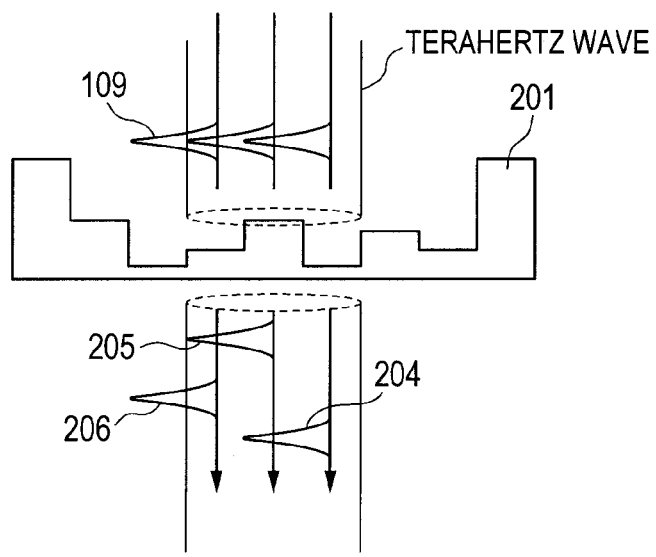
FIG. 2B is a sectional view along line 2B-2B in FIG. 2A.

FIG. 2B is a sectional view along line 2B-2B of a resin sheet 201. As illustrated in the figure, the modulation region 112 of the resin sheet 201 is made of a member that has a different thickness for each pixel region. Since the different refractive index is different between atmosphere and resin, the propagation distance of the terahertz wave changes depending on the thickness of the member, and as a result, the propagation time also changes. Assuming that, as illustrated in the figure, the terahertz wave 109 from the object reaches each pixel region in the same timing, the modulation unit 103 emits terahertz waves (204, 205, and 206) each having a different propagation time, and thus, a pulse train is generated. The resin sheet 201 is desirably made of a material having less loss with respect to the terahertz wave. For example, polyethylene, polycarbonate, cycloolefin, and the like may be applied.

The difference in thickness of the members for each pixel region is desirably to the extent required to separate a pulse train of terahertz waves. The difference in thickness of the members for each pixel region is preferably to the extent required to generate a time difference of about half-value width of a pulse between the pulses regarding the pulse width of the terahertz wave to be used. For example, assuming that the half-value width of the terahertz wave pulse to be used is 300 femtoseconds and the refractive index of the member is 1.5, the difference in thickness of the members is about 60 μm. Note that the difference in thickness of the members may be to the extent required to generate a time difference of half-value width or less of a terahertz wave pulse between the pulses. As such an example, a reference wave is used to perform deconvolution on a pulse train of terahertz waves to be used to calculate an impulse pulse train. In such example, the difference in thickness of the members is not a half-value width of a terahertz wave pulse, but to the extent required to generate a time difference of about a half-value width of an impulse signal obtained by the above calculation between the pulses. The difference in thickness of the members at this time is several μm.

The stage 202 holds the resin sheet 201 and changes the position of the modulation region 112 in a surface direction with respect to an incident direction of the terahertz wave irradiation region 113. A movement of the modulation region 112 changes a thickness distribution of the members included in the terahertz wave irradiation region 113. As a result, various patterns of pulse trains are emitted from the modulation unit 103 by adjusting the position of the irradiation region 113 of the terahertz wave radiating the modulation region 112. The driver 203 adjusts the position of the stage 202. In a case in which a correspondence between a position of the stage 202 and a modulation pattern for use in the present apparatus is stored, the modulation patterns can be switched by a control amount of the driver 203.

Although The above description has focused on a configuration of the transmission type modulation unit 103 as a combination of the resin sheet 201 and the stage 202, the configuration of the modulation unit 103 is not limited to this. Any configuration may be used as long as spatial modulation can be performed by causing the terahertz wave 109 from the object 108 to transmit through the modulation unit 103 and partially changing the propagation distance thereof. For example, the resin sheet 201 may be replaced with a ceramic or semiconductor substrate. Further, despite that in the above described transmission type modulation unit 103 performs spatial modulation on the terahertz wave 109 from the object by adjusting the thickness of the member of the modulation region 112, the thickness of the member may instead be uniform. Since the propagation distance of the terahertz wave changes depending on the refractive index of the member, the refractive index distribution of the terahertz wave irradiation region 113 can be adjusted by controlling an alignment state of liquid crystal material and a particle distribution by electrophoresis. In this case, the refractive index distribution of the terahertz wave irradiation region 113 can be adjusted electrically, whereby the time required to switch the modulation pattern can be shortened and the visualization speed can be improved. Further, since the refractive index distribution of the terahertz wave irradiation region 113 can be adjusted electrically, the stage 202 for switching the modulation pattern can be omitted, thereby reducing the size of the apparatus.

The above described transmission type modulation unit 103 performs spatial modulation on the terahertz wave from the object by means of a transmitting member having a different propagation distance of the terahertz wave. In this configuration, spatial modulation can implemented by inserting the modulation unit 103 in the terahertz wave propagation path, whereby the distance of the terahertz wave propagation path for performing spatial modulation can be minimized. Thus, this configuration exerts an effect of simplifying the apparatus configuration.

Figure 3A:
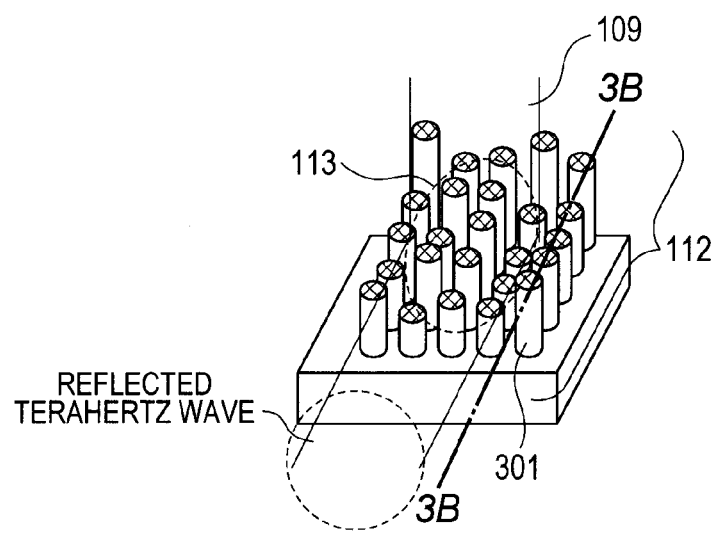
FIG. 3A describes a configuration example of a reflection type modulation unit.
Figure 3B:
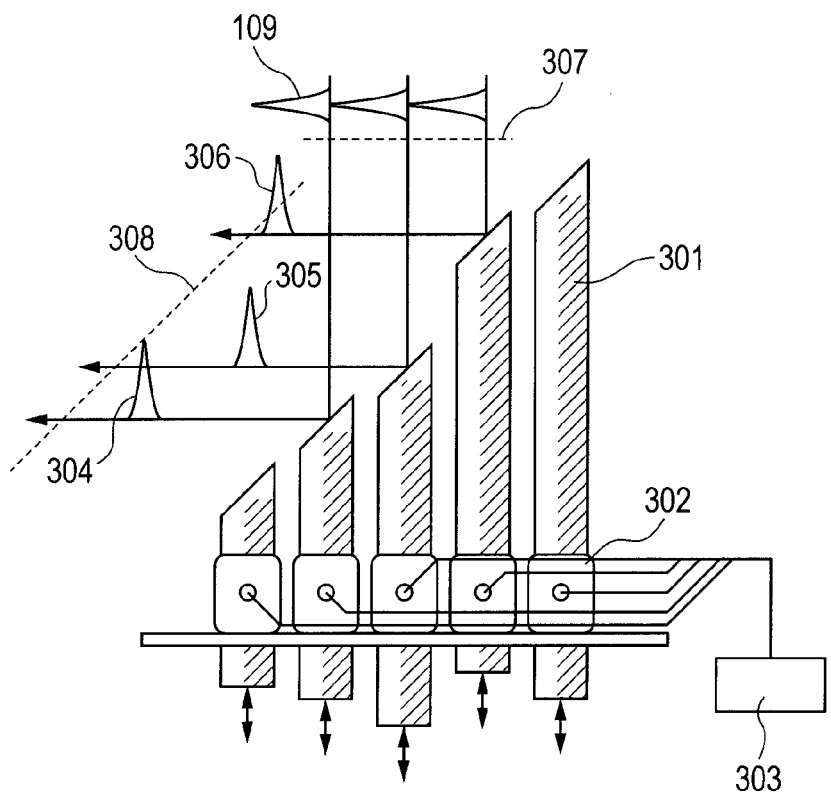
FIG. 3B is a sectional view along line 3B-3B in FIG. 3A.

FIG. 3A illustrates a configuration example of a reflection type modulation unit 103. As illustrated in FIG. 3B which is a sectional view along line 3B-3B in FIG. 3A, the modulation unit 103 includes a rod 301, an actuator 302, and a driver 303. The rod 301 in FIG. 3A has a reflecting member in an end portion for reflecting the terahertz wave 109 from the object 108. This reflecting member is desirably a metal surface having a roughness of about 1/20·λ, or less with respect to the shortest wavelength λ of the terahertz wave to be used. Further, the metal surface may have a dielectric protective film for protecting the metal surface and a multilayer film structure for improving the reflection efficiency. The end portion of the rod 301 is cut in a direction of a reflection with respect to the incident direction of the terahertz wave 109 from the object. As described in the transmission type modulation unit 103, the sectional area of the rod 301 is defined by the overlapping region A and the distance D from the object 108 up to the modulation region 112 of the modulation unit 103. Although the rod 301 is illustrated in a cylindrical shape in FIGS. 3A and 3B, but the shape of the rod 301 is not limited to this, and it may be in a polygonal shape. The modulation region 112 is configured to include a plurality of rods 301. The modulation region 112 has a size of covering at least the terahertz wave irradiation region 113. FIG. 3A illustrates an embodiment in which the terahertz wave 109 from the object is incident in a longitudinal direction of the rod 301 and the reflected terahertz wave is emitted at an angle of 90 degrees with respect to the incident direction. The emission angle is not limited to this, and it may be selected as needed according to the apparatus specification.

FIG. 3B is a sectional view along line 3B-3B in FIG. 3A illustrating the modulation unit 103. As illustrated in the figure, the rods 301 in the modulation region 112 are arranged such that each end portion of the rods 301 is substantially aligned at the emission angle of the reflected terahertz wave. When each rod 301 is moved in the longitudinal direction of the rod 301 by the actuator 302, the propagation distance of the terahertz wave changes depending on the position of the rod 301, and thus the propagation time changes accordingly. As illustrated in the figure, an assumption is made that the terahertz wave 109 from the object reaches the rod 301 constituting each pixel region in the same timing with respect to an end face shape 307 of the terahertz wave. At this time, the modulation unit 103 emits the terahertz waves (304, 305, and 306) each having a different propagation time with respect to the end face shape 308 of the reflected terahertz wave. As a result, a pulse train is generated.

As described above, the actuator 302 changes the position of the rod 301 in the modulation region 112 to the longitudinal direction of the rod 301. The actuator 302 may desirably have a positioning precision from several μm to sub μm. For example, a piezo element or a stepping motor may be applied. The height distribution of the rod 301 included in the terahertz wave irradiation region 113 can be changed by individually adjusting the position of the rod 301 in the modulation region 112. Thus, an adjustment of the height distribution of the rod 301 causes various patterns of pulse trains to be emitted from the modulation unit 103. Note that the height of the rod 301 may desirably be adjusted to a positional relation in which the terahertz waves (304, 305, and 306) reflected from the rod 301 are not completely shielded. As described in the transmission type modulation unit 103, the difference in height of the rod 301 to be adjusted may desirably be to the extent required to separate the pulse train of terahertz waves. For example, assuming that the half-value width of the terahertz wave pulse to be used is 300 femtoseconds, the difference in height of the rod 301 is about 90 μm. As is also described in the transmission type modulation unit 103, an embodiment in which a reference wave is used to perform deconvolution on a pulse train of terahertz waves to be used to calculate an impulse pulse train may be applied. The driver 303 controls the operation of the actuator 302 and adjusts the height of the rod 301. A correspondence between a control amount of the actuator 302 and a modulation pattern for use in the present apparatus may be stored in a memory, and the modulation patterns can be switched by a control amount of the driver 303.

In the above described reflection type modulation unit 103, spatial modulation is performed on the terahertz wave from the object using a plurality of reflecting members provided in the modulation unit 103 to adjust the propagation distance of the terahertz wave reflected by the modulation unit 103. This embodiment eliminates the need to propagate the terahertz wave inside the member in order to perform spatial modulation, whereby loss of the terahertz wave due to spatial modulation can be suppressed. Thus, this embodiment can increase the detection sensitivity of the apparatus and exerts an effect of improving the image contrast to be formed.

(Adjustment Unit 105)

Referring now back to FIG. 1A, the adjustment unit 105 adjusts the position on a time axis of the time waveform of the terahertz wave by referring to the modulation pattern used by the modulation unit 103. Specifically, the adjustment unit 105 converts, to a time amount, the change amount of the propagation distance of the terahertz wave for each pixel corresponding to the used modulation pattern. In other words, based on the time amount, the adjustment unit 105 adjusts the position on a time axis of the first time waveform of the first terahertz wave and the second time waveform of the second terahertz wave stored in the waveform generating unit 102. In the present description, the adjusted first time waveform is referred to as a third time waveform and the adjusted second time waveform is referred to as a fourth time waveform. The adjustment unit 105 outputs the third time waveform and the fourth time waveform.

Figure 4A:
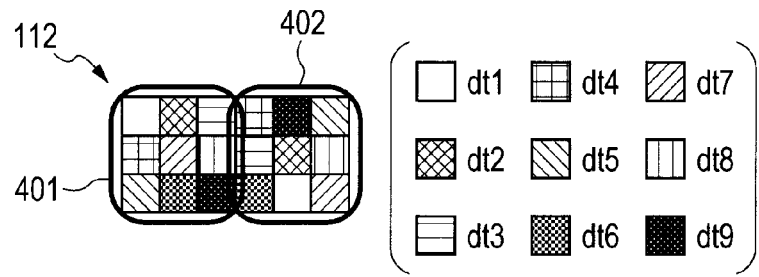
FIG. 4A illustrates a configuration of a modulation region 112 of a modulation unit 103.

Referring to figures, the operation of the adjustment unit 105 will be described. Here, it is assumed that the transmission type modulation unit 103 described in FIG. 2A is used. FIG. 4A illustrates a configuration of the modulation region 112 of the modulation unit 103 for use in the description. The modulation region 112 includes 18 pixel regions. Each pixel region has a change amount of propagation distance. A total of nine change amounts: dt1, dt2, dt3, dt4, dt5, dt6, dt7, dt8, and dt9 are available. These change amounts of the propagation distance are adjusted by the thickness of the resin sheet 201. For example, when cycloolefin with a refractive index of 1.5 is used as the resin sheet 201, one picosecond corresponds to a thickness of 200 μm. As illustrated in FIG. 4A, the modulation region 112 is configured such that these pixel regions are randomly arranged. Here, an assumption is made that the irradiation region 113 of the terahertz wave 109 from the object 108 radiating the modulation region 112 is made of 3×3 pixel regions. Specifically, when the modulation region 112 is irradiated with a single pulse terahertz wave, up to nine pulse trains are emitted from the modulation unit 103. Hereinafter, the operation flow of the apparatus including the operation of the adjustment unit 105 will be described. The following description of the operation flow will focus on a central pixel region of each modulation pattern.

(1) In FIG. 4A, the position of the modulation region 112 of the modulation unit 103 is adjusted and the terahertz wave is emitted to the position of the first modulation pattern 401.

(2) The modulation unit 103 emits the first terahertz wave 110 of FIG. 1A. Since the first modulation pattern 401 includes each one of the nine pixel regions from dt1 to dt9, nine pulse trains are emitted corresponding to the first terahertz wave 110.

(3) The detection unit 101 detects the first terahertz wave 110 and the waveform generating unit 102 generates the first time waveform 403.

(4) The adjustment unit 105 refers to the used first modulation pattern 401 and acquires the change amount of the propagation distance of the pixel region of interest. In this example, an attention is paid to the central pixel region of the first modulation pattern, and hence the change amount of the propagation distance of the terahertz wave propagating the central pixel region is dt7.

(5) The adjustment unit 105 converts the acquired change amount of the propagation distance to a time amount. When the transmission type modulation unit 103 is used, the change amount is converted to the time amount by taking into account the refractive index of each pixel region.

Figure 4B:
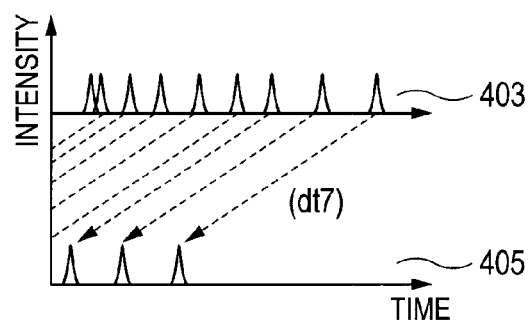
FIG. 4B illustrates how an adjustment unit adjusts a position on a time axis of a first time waveform to calculate a third time waveform.

(6) Based on the time amount obtained in step (5), as illustrated by a specific example in the case of the number of pixels: n=2 and m=2 in FIG. 4B, the adjustment unit 105 adjusts the position on a time axis of the first time waveform 403 stored in the waveform generating unit 102 and calculates the third time waveform 405. Specifically, the position on a time axis of the first time waveform 403 is shifted by the time amount obtained in step (5) in an opposite direction of a time proceeding direction (along a time axis). In this example, the position is shifted by a time amount corresponding to the change amount dt7.

(7) In FIG. 4A, the position of the modulation region 112 of the modulation unit 103 is adjusted and the terahertz wave is emitted to the position of the second modulation pattern 402.

(8) The modulation unit 103 emits the second terahertz wave 111 in FIG. 1A. Since the second modulation pattern 402 includes each one of the nine pixel regions from dt1 to dt9, nine pulse trains are emitted corresponding to the first terahertz wave 111.

(9) The detection unit 101 detects the second terahertz wave 111, and the waveform generating unit 102 generates the second time waveform 404.

(10) The adjustment unit 105 refers to the used second modulation pattern 402 and acquires the change amount of the propagation distance of the pixel region of interest. In this example, an attention is paid to the central pixel region of the second modulation pattern, and hence the change amount of the propagation distance of the terahertz wave propagating the central pixel region is dt2.

(11) The adjustment unit 105 converts the acquired change amount of the propagation distance to a time amount. When the transmission type modulation unit 103 is used, the change amount is converted to the time amount by taking into account the refractive index of each pixel region.

Figure 4C:
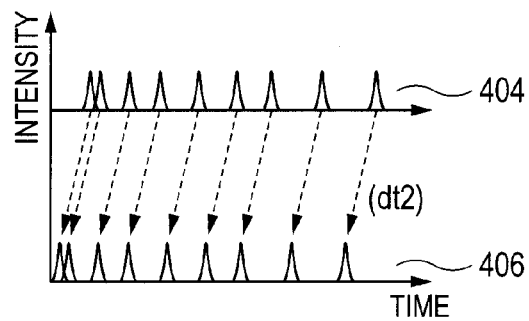
FIG. 4C illustrates how the adjustment unit adjusts the position on the time axis of the third time waveform to calculate a fourth time waveform.

(12) Based on the time amount obtained in step (11), as illustrated by a specific example in the case of the number of pixels: n=2 and m=2 in FIG. 4C, the adjustment unit 105 adjusts the position on a time axis of the second time waveform 404 stored in the waveform generating unit 102 and calculates the fourth time waveform 406. Specifically, the position on a time axis of the second time waveform 404 is shifted by the time amount obtained in step (12) in an opposite direction of a time proceeding direction (along a time axis).

The above operation is performed for each pixel region. That is, the third time waveform 405 and the fourth time waveform 406 are obtained for each pixel region. Although two modulation patterns are used in the above description, the three or more modulation patterns may be used instead. Further, in the operation flow, although the apparatus changes the modulation pattern and then adjusts the time waveform, the operation flow is not limited to this order. For example, the results of generating the time waveform of the terahertz wave with a change in modulation pattern may be sequentially stored in the waveform generating unit 102, and when all changes of the modulation patterns are completed, the adjustment unit 105 may adjust the time waveform. Alternatively, generation of the time waveform by the waveform generating unit 102 may be performed in parallel to adjustment of the time waveform by the adjustment unit 105.

Although only the position of the time waveform is adjusted in the steps (6) and (12) for time axis adjustment, a step of compensating for an effect on a pixel region during propagation in the pixel region may be additionally provided. For example, when a transmission type modulation unit 103 is used, a change in pulse shape by absorption or diffusion due to propagation in the pixel region may be compensated. Alternatively, the position in which an echo pulse occurs due to reflection of a terahertz wave inside the member may be determined in advance to remove the echo pulse. When a reflection type modulation unit 103 is used, an effect on a pulse shape and an echo pulse due to a protective film and multilayer film of the reflecting member may be removed. Since these effects can be known in advance, these may be stored, and based on the stored information, a changed pulse shape may be returned to the original shape. The use of such steps can suppress an effect due to modulation unit 103, which exerts an effect of reducing deterioration of contrast and generation of ghost during imaging.

The first modulation pattern 401 and the second modulation pattern 402 may be implemented by a preset modulation pattern or may be randomly selected. When a preset modulation pattern is used, information of the modulation pattern for use in adjusting the time waveform can be prefetched. Thus, this embodiment exerts an effect of facilitating the improvement of the operation speed of the apparatus. When the modulation pattern is randomly selected, it is durable to use a monitor unit to be described later to determine the modulation pattern.

(Monitor Unit 104)

Referring again back to FIG. 1A, the monitor unit 104 monitors the state of the aforementioned modulation unit 103 and determines the used modulation pattern. For example, the monitor unit 104 determines the used modulation pattern from a control state of the drivers (203 and 303) provided in the transmission type or reflection type modulation unit 103. Alternatively, the state of the modulation region 112 may be measured by a camera or a three-dimensional measuring instrument, and based on the results, the used modulation pattern can be determined. Thus, in this embodiment, the monitor unit 104 monitors the state of the modulation unit 103 and, based on the monitored results, it determines the modulation pattern to which the adjustment unit 105 refers. When the modulation pattern is continuously determined from the state of the monitor unit 104, it is possible to prevent using a modulation pattern different from the used modulation pattern for adjusting the position on a time axis of the time waveform. Thus, this embodiment exerts an effect of stabilizing the apparatus operation.

Alternatively, an embodiment without using the monitor unit 104 may be provided. In such embodiment, a unit (referred to as a pattern storage unit in the present description) of storing a modulation pattern to be used in advance may desirably provided thereto. The modulation unit 103 performs spatial modulation on the terahertz wave 109 from the object 108 according to the modulation pattern stored in the pattern storage unit. Further, the adjustment unit 105 adjusts the time waveform of the terahertz wave according to the modulation pattern stored in the pattern storage unit. Thus, the modulation unit 103 performs spatial modulation on the terahertz wave 109 from the object based on a preset modulation pattern which is stored in advance in the pattern storage unit, and the adjustment unit 105 refers to the modulation pattern stored in the pattern storage unit and adjusts the position on a time axis of the time waveform. Consequently, the adjustment unit 105 can prefetch the information of the modulation pattern for use in adjusting the time waveform, and the operation speed of the apparatus can be improved.

(Addition Unit 106)

Figure 4D:
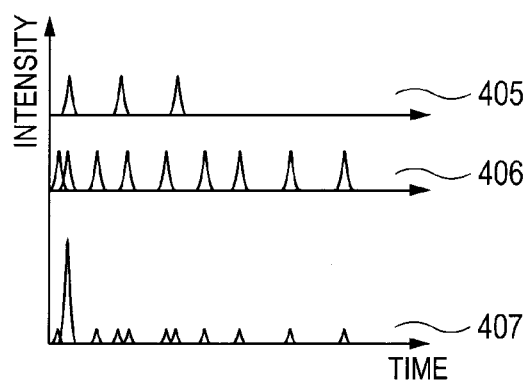
FIG. 4D illustrates a configuration of the modulation region 112 of the modulation unit 103.

The addition unit 106 adds the third time waveform 405 and the fourth time waveform 406 obtained from the adjustment unit 105. Depending on the apparatus configuration, these time waveforms may be added and averaged. In the present description, such processes, including a simple addition, is referred to as an addition processing. In this embodiment, an adding and averaging will be referred. This operation is performed for each pixel to be imaged. Specifically, the third time waveform 405 and the fourth time waveform 406 of a pixel region corresponding to a pixel are acquired to be added and averaged. When a plurality of time waveforms is added and averaged, a signal overlapping portion is emphasized and randomly generated signals like noise cancel each other to be planarized. As a result, an SN ratio of the signal is improved in proportion to the square root of the number of additions. The present apparatus uses the adjustment unit 105 to make an adjustment such that the signal of a pixel region of interest appears in the same position on a time axis. Accordingly, the signals other than the pixel region of interest are arranged in various positions on a time axis according to the adjustment amount of the adjustment unit 105. As a result, the signal of a pixel region of interest is emphasized and the other signals are planarized, whereby the signal of the pixel region of interest is extracted. This appearance is illustrated in FIG. 4D. As described above, in FIGS. 4B to 4D, of the modulation patterns, an attention is paid to the signal of the central pixel region. When the third time waveform 405 and the fourth time waveform 406 calculated in FIGS. 4B and 4C are added and averaged, the added and averaged time waveform 407 emphasizes the signal in the overlapping portion.

(Image Forming Unit 107)

The image forming unit 107 performs imaging on the object 108 from the time waveform calculated by the addition unit 106. Specifically, the image forming unit 107 arranges the time waveform from each pixel region on a pixel to be imaged. Then, the image forming unit 107 converts the time axis of each time waveform to a distance to form a three dimensional image as the depth direction information of the object 108. In the imaging on the object 108 by the image forming unit 107, there may be included a step of performing deconvolution using a reference signal of the apparatus measured in advance to improve the resolution in the depth direction. For example, a mirror may be installed in a position of the object 108, the time waveform of the terahertz wave obtained at the time without the object 108 can be used as the reference signal. Alternatively, a reflecting object having substantially the same outer shape of the object 108 to be measured may be arranged and the time waveform of the terahertz wave at this time can be used as the reference signal. When the reference signal is obtained, the aforementioned modulation unit 103 may be used to obtain the reference signal of each pixel region.

When the time axis of the time waveform is converted to a distance, there may be a configuration in which a refractive index is calculated from information on the physical property to compensate for an effect of reducing the wavelength by the refractive index. The information on the physical property can be obtained from a change in terahertz wave pulse reflected from an interface inside the object 108. Alternatively, spectrum information may be obtained from the terahertz wave actually reflected from the interface. If the internal structure of the object 108 is known in advance, information on the internal structure may be used to compensate for an effect of reducing the wavelength of the terahertz wave.

As described above, in the apparatus and the method of the present embodiment, the propagation distance of the terahertz wave from the object to the detection unit is changed for each pixel and spatial modulation on the terahertz wave from the object is performed. The spatial modulation patterns are changed each time the time waveform is measured and the detection units such as detectors less than the number of pixels measure the time waveform. In visualization, the modulation pattern is referred to for adjusting the position on a time axis of the time waveform of the terahertz wave for each pixel such that each pixel has the same propagation distance of the terahertz wave. The aforementioned processing is performed on the measured time waveform, and the processed time waveforms are added and averaged for each pixel, thereby to extract and visualize the time waveform of each pixel. Here, the spatial modulation on the terahertz wave is implemented without using a spatial distribution depending on the presence or absence of a terahertz wave, and it is implemented by changing the time the terahertz wave takes to reach each pixel of the detection unit. Consequently, the terahertz wave is not shielded when spatial modulation is performed on the terahertz wave, whereby reduction of the signal intensity of the terahertz wave can be suppressed. As a result, the time waveforms of a plurality of pixels can be measured while maintaining the detection sensitivity of the terahertz waves.

Figure 8A:
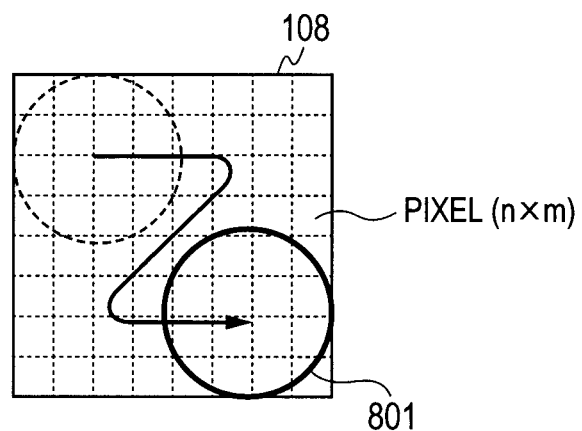
FIG. 8A describes another embodiment of an observation method according to the present invention.
Figure 8B:
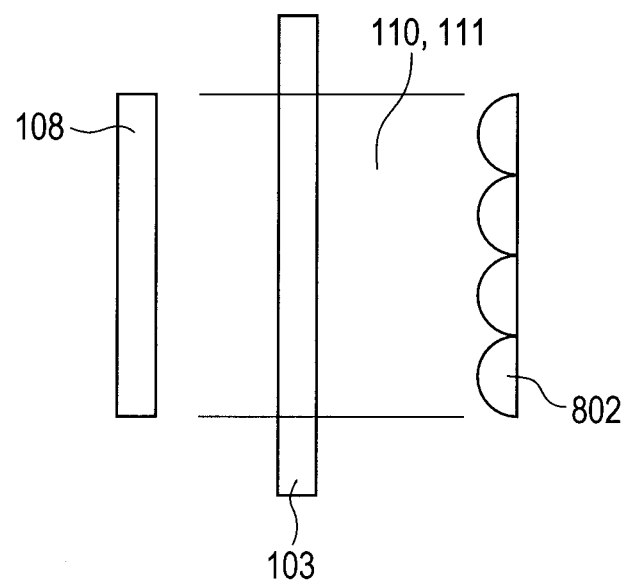
FIG. 8B describes yet another embodiment of the observation method according to the present invention.

Note that, in the present apparatus and the method, when the object 108 is observed, the terahertz wave 109 from the object propagating from an observation region are not limited to be collectively acquired. For example, as illustrated in FIG. 8A, the observation region 801 may be relatively moved by the terahertz wave with respect to the object 108 for scanning. At this time, the image forming unit 107 monitors the position of an observing region and thereby joins together the images obtained from the observation region 801. Further, although in the above description the object 108 and the detection unit 101 are paired with each other, a plurality of detectors 802 is provided for one object 108 as illustrated in FIG. 8B and the observation region 801 can be divided to acquire the image. When the observation region 801 for the object 108 is restricted as such, the terahertz wave intensity for unit area can be increased and unwanted external electromagnetic noise can be suppressed from being mixed. As a result, the SN ratio of a signal can be increased and the detection sensitivity can be improved.

More specific embodiments of the image forming apparatus and the method of the present invention will hereinafter be described with reference to the accompanying drawings. Note that the description overlapping the above description will be omitted.

(First Embodiment)

Figure 5:
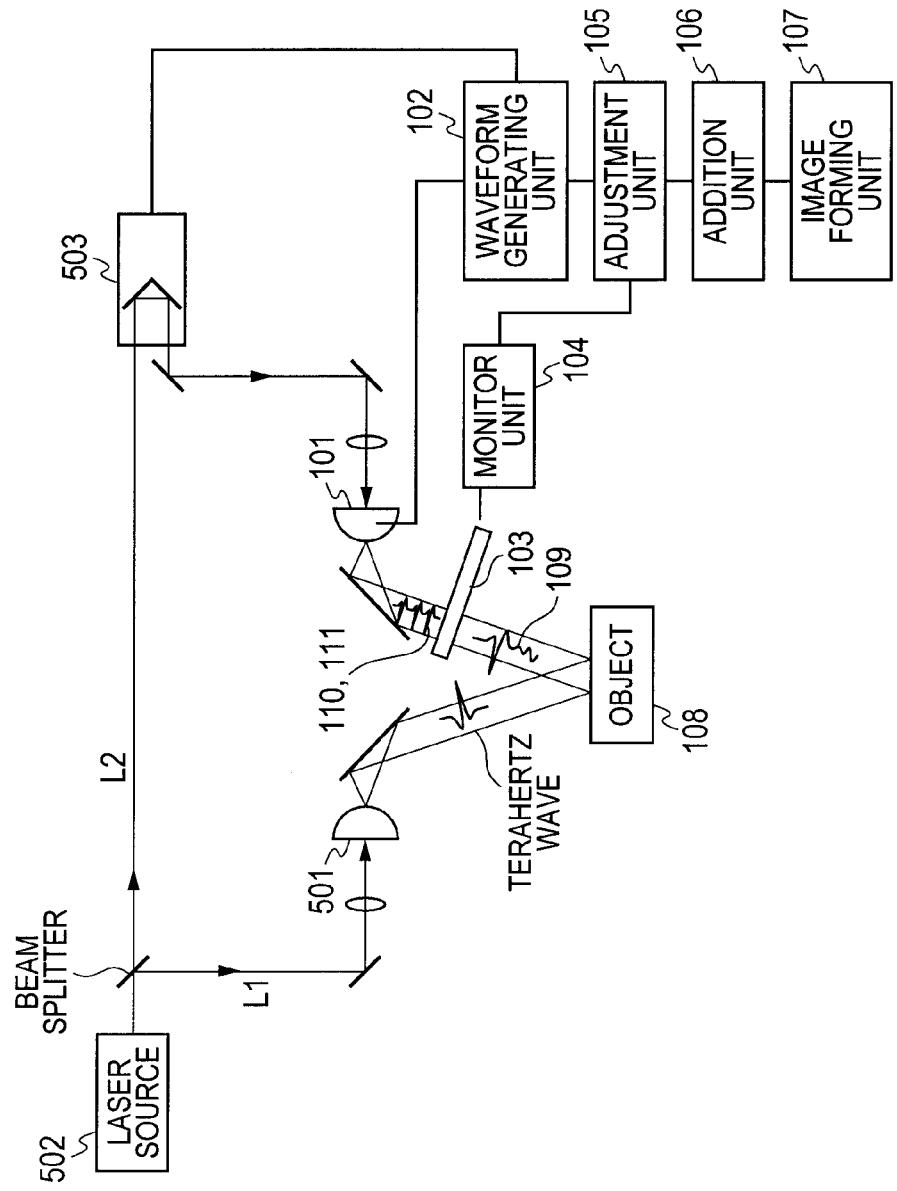
FIG. 5 describes a configuration of a first embodiment.

FIG. 5 is a schematic configuration view of an image forming apparatus and a method of a first embodiment. A generation unit 501, a laser source 502, and a delay optical unit 503 are added to the aforementioned apparatus configuration. As is easily understood from FIG. 5, this image forming apparatus is a reflection type apparatus configuration in which a terahertz wave is reflected by the object 108.

The generation unit 501 generates a pulsed terahertz wave. The principle of generating the terahertz wave by the generation unit 501 includes a method of using instantaneous current and a method of using interband transition of a carrier. Examples of the method of using instantaneous current include a method of generating a terahertz wave by irradiating a surface of a semiconductor or an organic crystal with excitation light. Specifically, excitation light is emitted in a state in which an electric field is applied to an element (photoconductive element) having an antenna pattern of metal electrodes formed on a semiconductor thin film. A PIN diode is also applicable. The method of using interband transition of a carrier in a gain structure includes a method of using a semiconductor quantum well structure. In this embodiment, an example of using the photoconductive element as the generation unit 501 will be described.

The laser source 502 outputs ultrashort pulse laser. In many cases, the pulse laser output from the laser source 502 has a pulse width of several 10 femtoseconds. The generation unit 501 and the detection unit 101 operate by emitting the ultrashort pulse laser to the semiconductor thin film to excite carriers. Thus, in the present description, the ultrashort pulse laser is also referred to as excitation light. As illustrated in FIG. 5, the excitation light is branched into two optical paths: L1 and L2. In the present embodiment, the excitation light passing through the optical path L1 reaches the generation unit 501. The excitation light passing through the optical path L2 reaches the detection unit 101 through a delay optical unit 503 to be described later. The wavelength of the laser source 502 changes depending on the wavelength absorbed by a semiconductor film of the generation unit 501 and the detection unit 101 to be used. Depending on the wavelength absorbed by the generation unit 501 and the detection unit 101, a wavelength conversion element may be inserted in a path of the optical path L1 or L2. The wavelength and the pulse width of the laser source 502 and the repetition frequency of the pulse laser are selected as needed according to the required apparatus specifications.

The delay optical unit 503 adjusts the propagation length of the excitation light and adjusts the timing of the excitation light irradiating the detection unit 101. Since, as described above, it is difficult to detect the terahertz wave in real time, the delay optical unit 503 adjusts a time difference between when excitation light is incident on the generation unit 501 and when the excitation light is incident on the detection unit 101, thereby to perform sampling measurement on the terahertz wave. The delay optical unit 503 may, for example, directly adjust the optical path length for propagating excitation light, adjust the effective optical path length. The method of directly adjusting the optical path length includes using a folded optical system for folding excitation light and a movable unit for moving the folded optical system in a folding direction. The method of adjusting the effective optical path length includes changing a time constant (refractive index) in the optical path for propagating excitation light. Note that the configuration of the delay optical unit 503 is not limited to this, and any configuration may be used as long as the configuration can adjust the time difference. In this embodiment, an example of using a folded optical system is described.

The laser source 502 outputs excitation light, and the excitation light is branched into optical paths L1 and L2 by a beam splitter. The excitation light propagating through the optical path L1 irradiates the generation unit 501, and the generation unit 501 generates a terahertz wave by the excitation light irradiation. The generated terahertz wave irradiates the object 108. The beam shape of the terahertz wave incident on the object 108 is adjusted to the extent required to cover a plurality of pixel regions for use in imaging. The terahertz wave is reflected by the object 108 to form a terahertz wave 109 from the object. The terahertz wave 109 from the object is affected by the internal structure and the physical property of the object 108. The modulation unit 103 uses a first modulation pattern and a second modulation pattern to perform spatial modulation on the terahertz wave 109 from the object to emit a first terahertz wave 110 and a second terahertz wave 111. Although the expression of the first terahertz wave 110 and the second terahertz wave 111 is used for the convenience of description, apparently more than two modulation patterns may be used.

The delay optical unit 503 receives the excitation light propagating through the optical path L2 and adjusts the timing of the excitation light incident on the detection unit 101. The detection unit 101 receives the excitation light and one of the first terahertz wave 110 and the second terahertz wave 111. The detection unit 101 detects a field intensity of the first terahertz wave 110 or the second terahertz wave 111 at a time when the excitation light is incident thereon. The waveform generating unit 102 refers to a change in propagation length by the delay optical unit 503 and an output from the detection unit 101, and generates a time waveform of the first terahertz wave 110 (first time waveform 403) and a time waveform of the second terahertz wave 111 (second time waveform 404).

As described above, the time waveform generated at this time has a pulse train shape in which pulses of each pixel region are mixed.

The monitor unit 104 monitors and outputs the modulation pattern used by the modulation unit 103. The adjustment unit 105 refers to this modulation pattern and the first time waveform 403 or the second time waveform 404 output from the waveform generating unit 102. Then, the adjustment unit 105 adjusts a position on a time axis of the terahertz wave for each pixel region to be used, and outputs a third time waveform 405 and a fourth time waveform 406. The signal input to the adjustment unit 105 is one pulse train: the first time waveform 403 or the second time waveform 404, and the signal output from the adjustment unit 105 includes a plurality of time waveforms of pulse trains for the number of processed pixels. Although in this embodiment the monitor unit 104 identifies the modulation pattern, the adjustment unit 105 may alternatively identify the modulation pattern. For example, the adjustment unit 105 may identify the modulation pattern from a control amount of the modulation unit 103 monitored by the monitor unit 104.

The addition unit 106 adds and averages a pulse train of the third time waveform 405 and a pulse train of the fourth time waveform 406 output from the adjustment unit 105. As a result, regarding the terahertz wave from the object 108, a response signal of the terahertz wave corresponding to each pixel region is extracted. This operation is performed for each pixel region to be used. As described above, the accuracy (SN ratio) of the extracted signal increases as the number of times of addition and averaging increases. The addition unit 106 outputs a response signal of the terahertz wave according to the number of processed pixel regions. The response signal of each terahertz wave output from the addition unit 106 is imaged by the image forming unit 107. The response signal of each terahertz wave is arranged in a position of each pixel region and the time axis of the terahertz wave is converted to a distance. When the distance conversion is performed by the speed of light, the obtained image is a three-dimensional image on which the physical property of the object 108 is superimposed. In other word, the physical property of the material is identified. An interface with color coding for each identified material may be used and the image forming unit 107 may output a tomographic image instead of a three-dimensional image.

Although the present embodiment has exemplified a reflection type arrangement in which the terahertz wave is reflected by the object 108, a transmission type arrangement in which the terahertz wave is transmitted through the object 108 may also be used. The modulation unit 103, which is interposed between the detection unit 101 and the object 108, may also be interposed between the generation unit 501 and the object 108. In this case, the modulation unit 103 modulates the propagation distance of the terahertz wave from the generation unit 501 to the object 108. In the present embodiment, the modulation unit 103 is interposed between the detection unit 101 and the object 108. Then, in comparison with an embodiment in which the modulation unit 103 is interposed between the generation unit 501 and the object 108, it is easier to reduce the distance between the modulation unit 103 and the detection unit 101. As described above, a reduction in distance between the modulation unit 103 and the detection unit 101 can suppress an increase of the beam diameter of the terahertz wave reaching the detection unit 101, which exerts an effect of reducing the size of the pixel region. Thus, with the above configuration, the present embodiment performs imaging inside the object 108.

(Second Embodiment)

Figure 6:
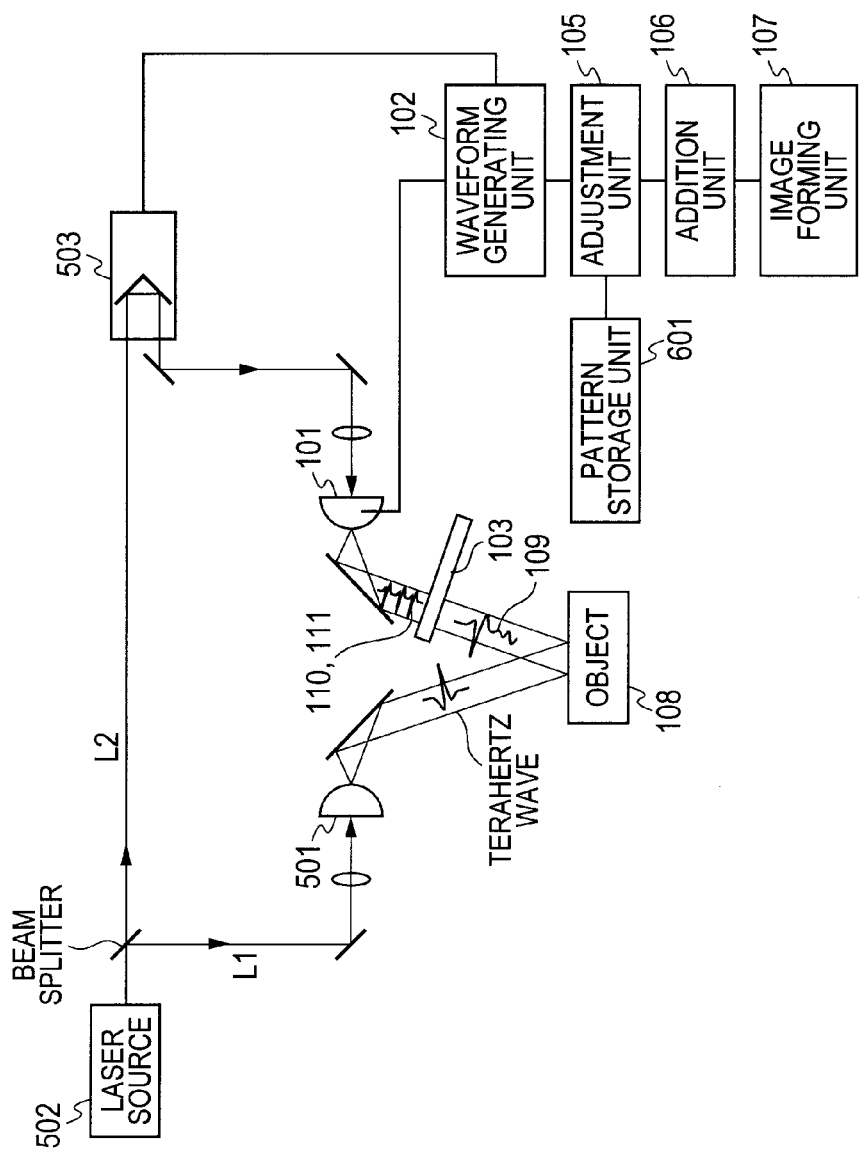
FIG. 6 describes a configuration of a second embodiment.

In a second embodiment, the modulation pattern used by the modulation unit 103 is identified. Note that the description overlapping the above description will be omitted. FIG. 6 is a schematic configuration view of an image forming apparatus of the present embodiment. The present embodiment is different from the first embodiment in that a pattern storage unit 601 is used instead of the monitor unit 104.

The pattern storage unit 601 stores the modulation patterns used by the modulation unit 103 and a preset order of the modulation patterns. The modulation unit 103 performs spatial modulation on the terahertz wave 109 from the object according to the preset order of the modulation patterns. The adjustment unit 105 adjusts the time waveform output from the waveform generating unit 102 by referring to the modulation patterns and the order stored in the pattern storage unit 601. In other word, the modulation unit 103 and the adjustment unit 105 performs processing separately by the preset modulation patterns and order. A trigger unit may newly be included for establishing synchronization between the modulation unit 103 and the adjustment unit 105 and the modulation pattern is changed according to a trigger signal of the trigger unit. Thus, a use of a different modulation pattern for processing between the modulation unit 103 and the adjustment unit 105 can be prevented, and system reliability can be increased.

Although the reflection type arrangement in which the terahertz wave is reflected by the object 108 is described in the present embodiment, the transmission type arrangement in which the terahertz wave is transmitted through the object 108 may also be used. With the above configuration, the present embodiment performs imaging inside the object 108.

(Third Embodiment)

Figure 7:
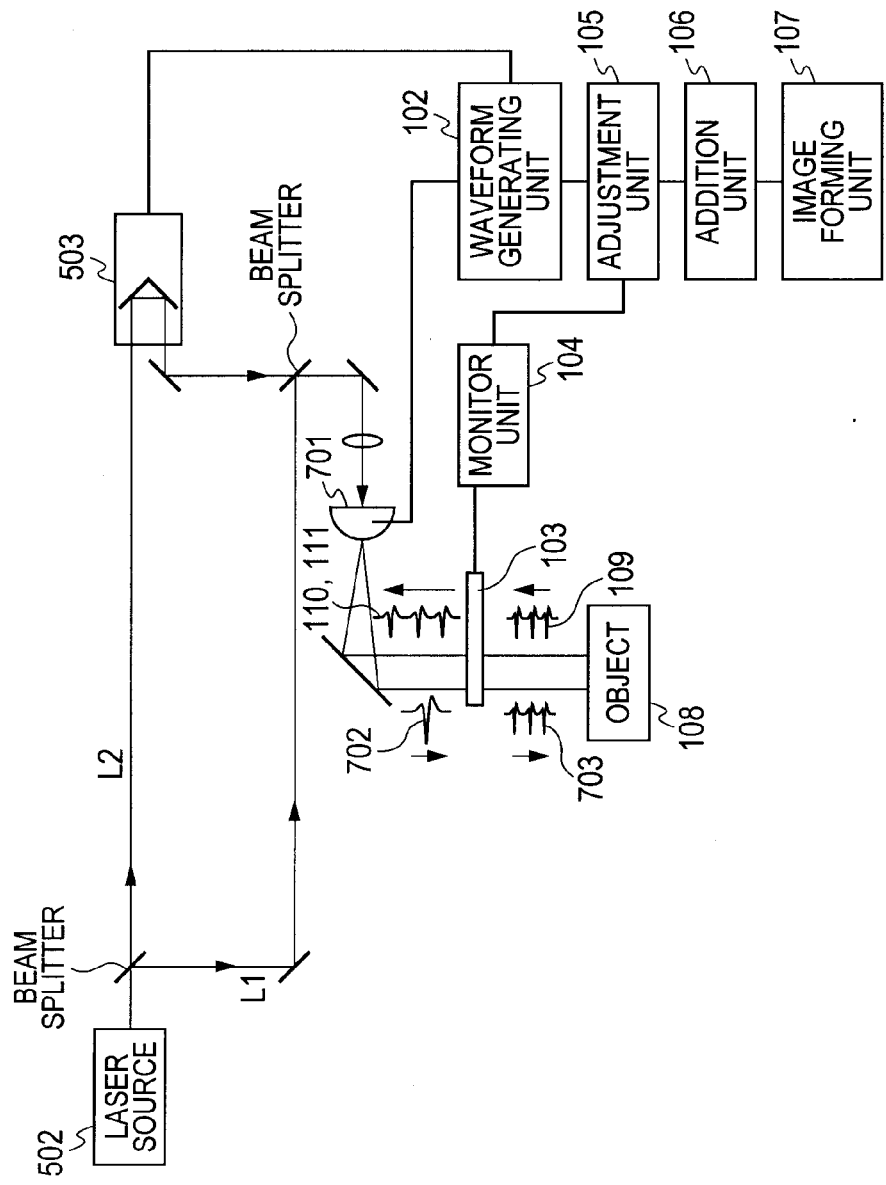
FIG. 7 describes a configuration of a third embodiment.

In a third embodiment, the generation unit and the detection unit are integrated. Note that the description overlapping the above description will be omitted. FIG. 7 is a schematic configuration view of an image forming apparatus of the present embodiment. The present embodiment is different from the above embodiments in that the generation unit is integrated with the detection unit into a generation detection unit 701.

The generation detection unit 701, which functions as a so-called transceiver, generates and detects the terahertz wave. Since the generation unit 501 and the detection unit 101 described above can also be made of an element having the same device structure, both generation and detection can be performed by the same device structure by adjusting the drive method. For example, when a photoconductive element is used as the generation detection unit 701, there is provided a circuit for detecting a current due to an electric field of a terahertz wave under the electric field used to generate the terahertz wave.

As illustrated in the figure, the excitation light generated by the laser source 502 is branched into optical paths L1 and L2 by a beam splitter. The excitation light of the optical path L1 is used for generating a terahertz wave. The excitation light of the optical path L2 is used for detecting the terahertz wave. The excitation light of the optical path L2 is subjected to adjustment of its propagation length by the delay optical unit 503, and then mixed again with the excitation light of the optical path L1 by another beam splitter. The time difference between the excitation light of the optical path L1 and the excitation light of the optical path L2 incident on the generation detection unit 701 is used to perform sampling measurement on the terahertz wave incident on the generation detection unit 701. The terahertz wave 702 generated by the generation detection unit 701 passes through the modulation unit 103 to form a terahertz wave 703. The terahertz wave 703 is subjected to spatial modulation by the modulation unit 103 to form a pulse train before reaching the object 108. The terahertz wave 703 irradiates the object 108, and a terahertz wave 109 from the object propagates along an incident propagation path of the terahertz wave 703. The terahertz wave 109 from the object is incident on the modulation unit 103. Then, the modulation unit 103 emits the first terahertz wave 110 and the second terahertz wave 111 according to the used modulation pattern.

According to the present embodiment, the modulation pattern used by the modulation unit 103 is monitored by the monitor unit 104. Then, the adjustment unit 105 refers to the monitor unit 104 to acquire the modulation pattern to be used to adjust the time waveform of the terahertz wave. Note that as described above, the monitor unit 104 may be replaced with the pattern storage unit 601.

Thus, with the above configuration, the image forming apparatus of the present embodiment performs imaging inside the object 108. Such a configuration allows the terahertz wave to be incident in a normal direction with respect to the surface of the object 108. Thus, this embodiment exerts an effect of being less affected by angular dependence of the terahertz wave on the object 108 during imaging. For example, the terahertz wave incident on the object 108 and the terahertz wave emitted therefrom propagate through a different path, whereby overlapping state of signals between adjacent pixels can be reduced. Further, the present embodiment eliminates the need to provide a step for compensating for the changed time axis of the terahertz wave when the terahertz wave is obliquely incident on the object 108 during imaging. Furthermore, the present embodiment eliminates the need to provide two elements of one for generation and one for detection of the terahertz wave to be used, which exerts an effect of reducing the size of the image forming apparatus and lowering the price thereof in an easy manner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-047735, filed Mar. 4, 2011, which is hereby incorporated by reference herein in its entirety.

What is claimed is:

1. A image forming apparatus for visualizing internal information of an object using time-domain spectroscopy, the apparatus comprising:
 a detection unit configured to detect a terahertz wave from the object;
 a generating unit configured to generate a time waveform of the terahertz wave from an output of the detection unit;
 a modulation unit configured to sequentially perform spatial modulation of terahertz waves for each pixel, on a propagation distance from an emission of the terahertz waves until reaching the detection unit, by using a first modulation pattern and a second modulation pattern, wherein the terahertz waves each correspond to a pixel of an object in a direction substantially perpendicular to a direction in which the terahertz wave penetrates inside the object, and to emit a first terahertz wave and a second terahertz wave;
 an adjustment unit configured to convert a change amount of the propagation distance of the terahertz wave for each pixel corresponding to the modulation pattern to a time amount, to adjust positions on a time axis of a first time waveform of the first terahertz wave and a second time waveform of the second terahertz wave from the generating unit based on the time amount, and to generate a third time waveform and a fourth time waveform; and
 an addition unit configured to perform an addition processing of the third time waveform and the fourth time waveform for each pixel.

2. The image forming apparatus according to claim 1, wherein the modulation unit is interposed between the object and the detection unit and the modulation unit performs spatial modulation on the propagation distance of the terahertz wave from the object to the detection unit.

3. The image forming apparatus according to claim 1, further comprising a monitor unit configured to monitor a state of the modulation unit and to output a modulation pattern according to the state of the modulation unit, wherein
 the adjustment unit is configured to refer to the modulation pattern output from the monitor unit and to adjust a position on a time axis of the time waveforms of the terahertz wave.

4. The image forming apparatus according to claim 1, further comprising a pattern storage unit configured to preliminarily store a first modulation pattern and a second modulation pattern to be used by the modulation unit, wherein
 the adjustment unit is configured to refer to the modulation pattern stored in the pattern storage unit and to adjust the position on a time axis of the time waveform of the terahertz wave.

5. The image forming apparatus according to claim 1, wherein the modulation unit includes a terahertz wave transmitting member in which the terahertz wave has a different propagation distance for each pixel forming an image.

6. The image forming apparatus according to claim 1, wherein the modulation unit includes a terahertz wave reflecting member configured to adjust the propagation distance of the terahertz wave from the object for each pixel forming an image.

7. An image forming method of visualizing internal information of an object using time-domain spectroscopy, the method comprising:
 a detection step of detecting a terahertz wave from the object by a detection unit;
 a waveform generating step of generating a time waveform of the terahertz wave from an output of the detection unit in the detection step;
 a modulation step of sequentially performing spatial modulation of terahertz waves for each pixel, on a propagation distance from an emission of the terahertz waves until reaching the detection unit, by using a first modulation pattern and a second modulation pattern, wherein the terahertz waves each correspond to a pixel of an object in a direction substantially perpendicular to a direction in which the terahertz wave penetrates inside the object, and emitting a first terahertz wave and a second terahertz wave;
 an adjustment step of converting a change amount of the propagation distance of the terahertz wave for each pixel corresponding to the modulation pattern to a time amount, adjusting positions on a time axis of a first time waveform of a first terahertz wave and a second time waveform of a second terahertz wave generated in the waveform generating step based on the time amount, and calculating a third waveform and a fourth time waveform; and an addition step of performing an addition processing of the third time waveform and the fourth time waveform for each pixel.

* * * * *